United States Patent
Ahn et al.

(10) Patent No.: US 6,330,350 B1
(45) Date of Patent: Dec. 11, 2001

(54) METHOD AND APPARATUS FOR AUTOMATICALLY RECOGNIZING BLOOD CELLS

(75) Inventors: Hyo Sok Ahn, Seoul (KR); Vassili A. Kovalev, Gomel (BY); Andrei Y. Grigoriev, Gomel (BY); Nikolai K. Myshkin, Gomel (BY)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 09/083,040

(22) Filed: May 22, 1998

(30) Foreign Application Priority Data

May 22, 1997 (KR) .................................................. 97-20018

(51) Int. Cl.[7] ...................................................... G06K 9/00
(52) U.S. Cl. ................................................................ 382/134
(58) Field of Search ........................... 382/128, 133, 382/134, 156, 165, 173, 181, 190, 192, 194, 224, 225, 226, 254, 286; 356/39; 600/309, 310, 322, 368; 436/519, 520, 66, 77

(56) References Cited

U.S. PATENT DOCUMENTS

| | | | |
|---|---|---|---|
| 4,097,845 | * 6/1978 | Bacus | 382/134 |
| 4,175,860 | 11/1979 | Bacus | 356/39 |
| 4,338,024 | 7/1982 | Bolz et al. | 356/23 |
| 4,581,223 | 4/1986 | Kass | 435/34 |
| 5,045,474 | 9/1991 | Becker et al. | 436/63 |
| 5,123,055 | 6/1992 | Kasdan | 382/134 |
| 5,541,064 | * 7/1996 | Bacus et al. | 435/6 |
| 5,741,213 | * 4/1998 | Kouchi et al. | 600/310 |
| 5,757,954 | * 5/1998 | Kuan et al. | 382/133 |
| 5,828,776 | * 10/1998 | Lee et al. | 382/133 |
| 5,911,000 | * 6/1999 | Shen | 382/134 |
| 6,151,405 | * 11/2000 | Douglass et al. | 382/133 |
| 6,169,816 | * 1/2001 | Ravkin | 382/128 |

FOREIGN PATENT DOCUMENTS

| | | |
|---|---|---|
| 0 424 871 | 5/1991 | (EP) . |
| WO 85/05450 | 12/1985 | (WO) . |
| WO 88/07199 | 9/1988 | (WO) . |

OTHER PUBLICATIONS

Harvey L. Kasdan, et al., Clinical Chemistry, vol. 40, No. 9, pp. 1850 to 1861, The White Iris Leukocyte Differential Analyzer for Rapid High–Precision Differentials Based on Images of Cytoprobe–Reacted Cells, Sep. 1994.

P. Joanne Cornblette, et al., Hematopathology, vol. 99, No. 1, pp. 72 to 81, "Evaluation of the Coulter STKS Five–Part Differential", Jan. 1991.

Stuart A. Bentley, et al., Hematopathology, vol. 100, No. 6, pp. 626 to 632, "A Parallel Evaluation of Four Automated Hematology Analyzers", Dec. 1993.

Malcolm L. Brigden, et al., Hematopathology, vol. 100, No. 6, pp. 618 to 625, "Evaluation of the Sysmex NE–8000", Dec. 1993.

Wolfgang Huebl, et al., Hematopathology, vol. 103, No. 2, pp. 167 to 170, "Precision and Accuracy of Monocyte Counting", Feb. 1995.

* cited by examiner

Primary Examiner—Andrew W. Johns
Assistant Examiner—Shervin Nakhjavan
(74) Attorney, Agent, or Firm—Oblon, Spivak, McClelland, Maier & Neustadt, P.C.

(57) ABSTRACT

A method and apparatus for automatically recognizing blood cells is provided. The method comprises obtaining image data of said blood cells, storing the image data of said blood cells in a memory, analyzing the image data of said blood cells and calculating a plurality of cell-characteristic parameter values for each of said blood cells, and recognizing each of said blood cells based on said plurality of cell-characteristic parameter values. In order to analyze the image data of blood cells, a group of nucleus pixels are first extracted from said stored image data and stored in the memory. The group of nucleus pixels are then segmented into individual nucleus clusters which represent each of the blood cells, and the data of the individual nucleus clusters are stored together with the associated cytoplasm data in the memory. Cell-characteristic parameter values for each of the blood cells are calculated based on its nucleus and associated cytoplasm data. The cell-characteristic parameter values are used in recognizing the blood cells.

6 Claims, 5 Drawing Sheets layers

METHOD AND APPARATUS FOR AUTOMATICALLY RECOGNIZING BLOOD CELLS

BACKGROUND OF THE INVENTION

1. Technical Field

The present invention relates in general to a method and apparatus for automatically recognizing blood cells, and in particular, to a method and apparatus for automatically recognizing blood cell type by using an image processing and a neural network mechanism in a computer system.

2. Description of the Related Art

Normal white blood cells observed in blood are largely divided into neutrophils, lymphocytes, monocytes, basophils, and eosinophils. The occurrence of immature blood cells such as a blast, a normoblast, and an immature granulocyte is indicative of blood diseases. Accordingly, blood cell recognition methods are required to diagnose blood diseases such as leukemia. The recognition of blood cells can be performed manually or automatically. In the manual recognition method, an examiner has to observe blood cells with a microscope, so it requires a lot of time and effort. This method is therefore inappropriate to be utilized in large hospitals.

In counting the white blood cells in a blood sample, two methods have been developed and used for an automatic blood recognizer. The first method, which has been predominantly used to date, employs the combination of cytochemistry, electric impedance (impedance method), and a light scatter principle (optical method). The impedance method is based on the measurement of changes in an electrical current which are produced by a particle, suspended in a conductive liquid, as it passes through an aperture of known dimensions. In the optical method, a suspension of a diluted blood sample passes through a laser light test section where the cells scatter the laser light at different angles, yielding information about the size, internal structure, granularity and surface morphology. However, this method can only either recognize the five kinds of normal white blood cells or classify the cells into three or four separate functions. For instance, U.S. Pat. No. 4,581,223 introduces new staining solutions for an improved cytochemical reaction but only five individual white blood cells are identified by selective use of basic quaternary metachromatic dye staining of blood at a controlled temperature. Immature cells are not recognized. International patent application PCT/US88/00960 describes an electronic counting method but this method also enables recognition of the above five kinds of white blood cells. The patent application, PCT/US85/00840 is directed to a reference control solution for an electronic threshold setting, but only for three separate white blood cell control portions (lymphocytes, mononuclear cells and granulocytes). Other examples are also available. See European Pat. EP 0 424 871 A1 and U.S. Pat. No. 5,045,474. The most well known blood cell counters based on above principles are the so-called Coulter Counter and Cell-Dyn Counter.

The second method is based on a pattern recognition method in which the white blood cells are recognized after their images have been acquired followed by digitized and image-processed in a computer. U.S. Pat. No. 4,338,024 discloses a method of obtaining still images of objects in a flow stream on a CCD camera. Successive results of investigation of this patent were published in Clinical Chemistry (40/9, pp. 1850–1861, 1994). In U.S. Pat. No. 4,175,860, a method and apparatus is disclosed for use in performing automated classification of cells using a set of images, i.e., a high resolution image of primarily the nucleus of a cell and a low resolution image of the total cell. The high-resolution image is processed to obtain information on the texture whereas the low-resolution image is processed to obtain information on the size, density and color of the cytoplasm and the nucleus. In U.S. Pat. No. 5,123,055, a method and apparatus is provided for automatically identifying the five kinds of white blood cells. However, so far, to applicant's knowledge, there has not been a simple and efficient method of differentiating the five kinds of white blood cells and critical immature blood cells. In addition, none of above mentioned references have disclosed a method of recognition which combines both a statistical module and a neural network.

SUMMARY OF THE INVENTION

It is therefore one object of the present invention to provide a method and apparatus for accurately recognizing normal white blood cells as well as immature blood cells.

In accordance with one aspect of the present invention, a method and apparatus for automatically recognizing blood cells is provided. The method comprises obtaining image data of said blood cells, storing the image data of said blood cells in a memory, analyzing the image data of said blood cells and calculating a plurality of cell-characteristic parameter values for each of said blood cells, and recognizing each of said blood cells based on said plurality of cell-characteristic parameter values. In order to analyze the image data of blood cells, a group of nucleus pixels are first extracted from said stored image data and stored in the memory. The group of nucleus pixels are then segmented into individual nucleus clusters which represent each of the blood cells and the data of individual nucleus clusters are stored together with the associated cytoplasm data in the memory. Cell-characteristic parameter values for each of the blood cells are calculated based on its nucleus and associated cytoplasm data. The cell-characteristic parameter values are used in recognizing the blood cells.

BRIEF DESCRIPTION OF THE DRAWINGS

The aforementioned aspects and other features of the invention are explained in the following description, taken in conjunction with the accompanying drawings wherein.

DETAILED DESCRIPTION OF PREFERRED EMBODIMENT

Figure 1:
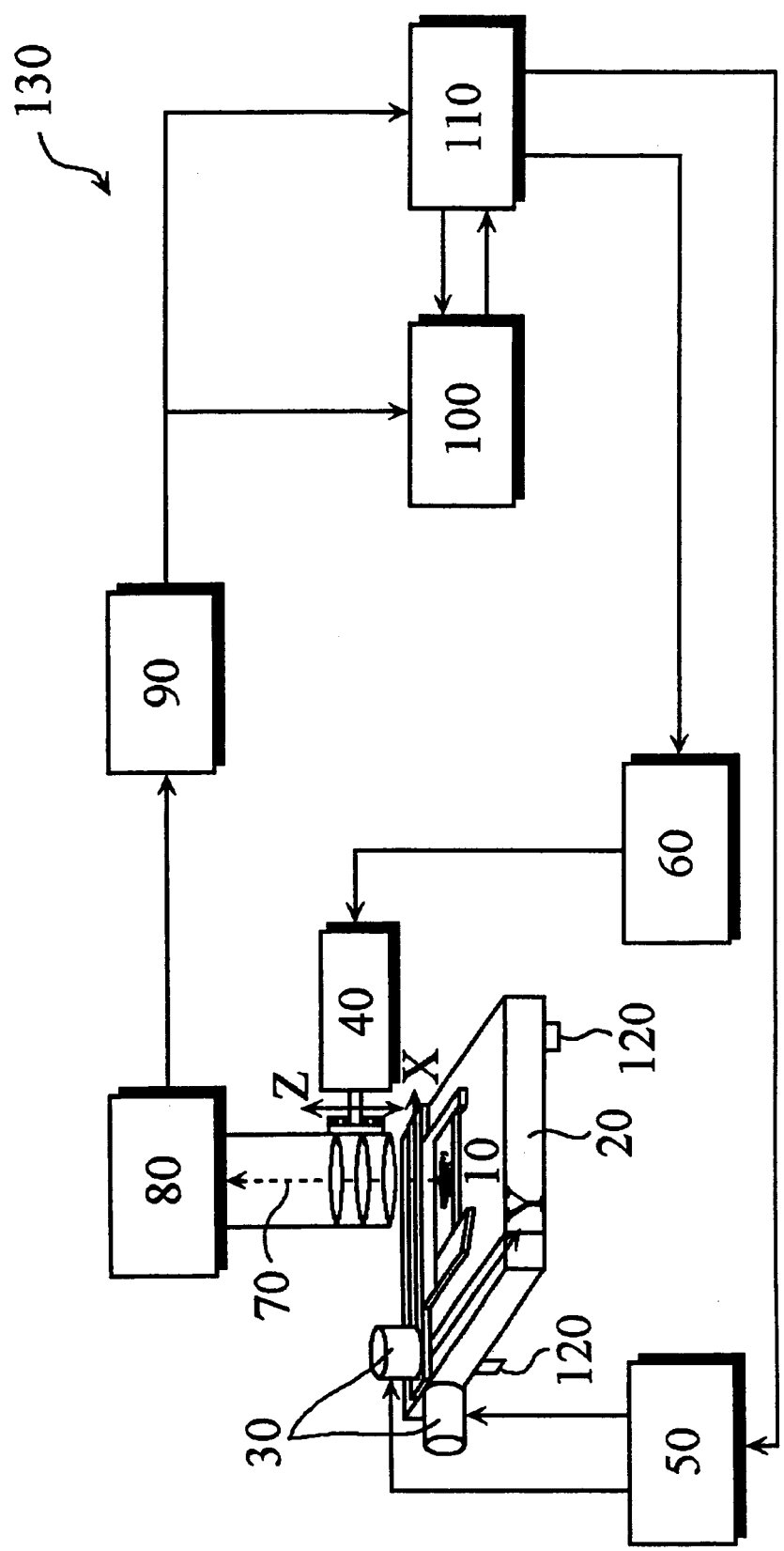
FIG. 1 illustrates a schematic block diagram of a blood cell automatic-recognition apparatus in accordance with one embodiment of the present invention.

FIG. 1 shows a schematic block diagram of a blood cell automatic-recognition apparatus in accordance with one embodiment of the present invention. As illustrated, the apparatus 130 includes a microscope stage 20 on which a blood smear is laid, horizontal driving means 30 for moving the stage 20 to the right or left direction, vertical driving means 40 for moving the stage 20 up and down, two controllers 50 and 60 for controlling the driving means 30 and 40, respectively, and a microscope lens 70 for enlarging an image of blood cells. Further, the apparatus 130 includes a color CCD camera 80 for converting the enlarged image of blood cells into the corresponding TV analog signals, an image capture board 90 containing an A/D converter, a memory 100 for storing the captured image data, control logic means 110 for recognizing blood cells by calculating cell-characteristic parameter values for each blood cell in the image data, and a limit switch 120 attached to the stage 20 for limiting the movement of the stage 20 to a certain degree.

The operation of the blood cell automatic-recognition apparatus 130 is described as follows: An examiner lays the blood smear 10 on the microscope stage 20 and sends an execution instruction to the control logic means 110. The control logic means 110 can control the horizontal driving means 30 to move the stage 20 right and left through the controller 50. A particular part of the moving image can be enlarged by a high magnification lens 70, the enlarged image is captured by the color CCD camera 80 in real time, and the captured image is converted into NTSC-based standard TV signals by the image capture board 90. The converted image data are stored in the memory 100. Sometimes, the miocroscope is out of focus in the process of obtaining an image since the magnification of the microscope is high. In such case, the control logic means 110 sends a control instruction to the controller 60. Then, the controller 60 controls the height of the stage 20 using the vertical driving means 40 so that the focus of the microscope can be adjusted. The control logic means 110 has two major functions: One is to control the movement of the stage 20 in each direction through controllers 50 and 60, and the other is to perform the calculation necessary to recognize the blood cells in the image data stored in the memory 100. The limit switch 120 can be installed below the stage 20. The switch 120 detects when the stage 20 moves out of the predetermined range and instructs the controller 50. The controller 50 then instructs the horizontal driving means 50 to stop moving the stage 20 or to move it in a reverse direction not to deviate from the predetermined range.

Figure 2:
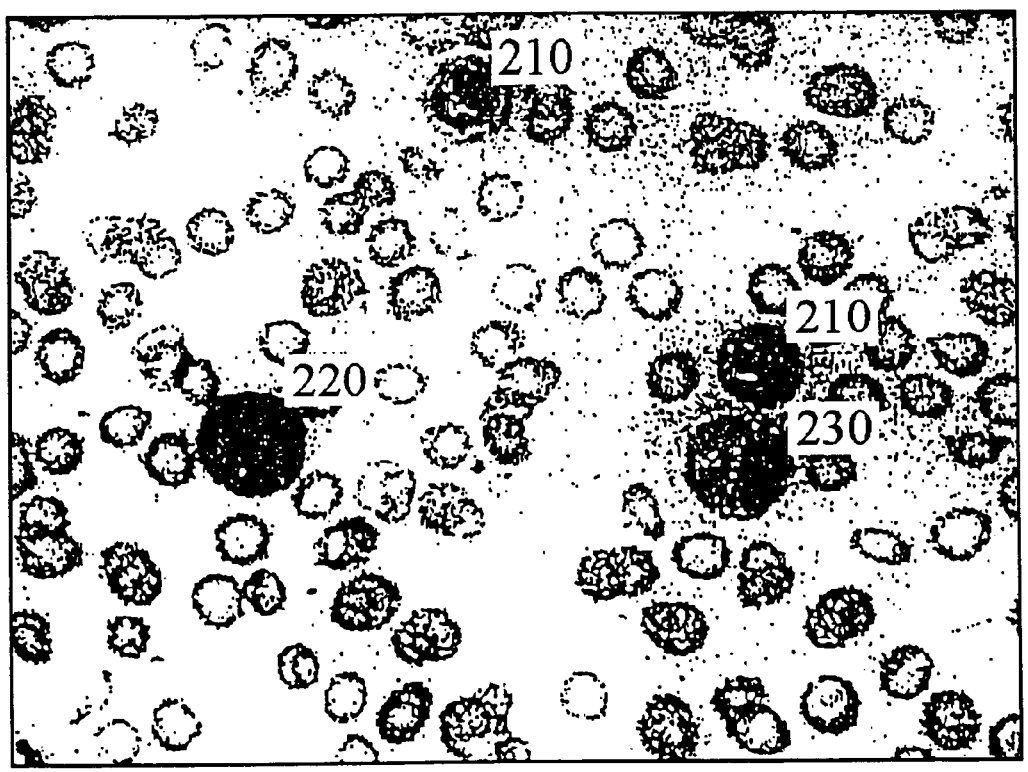
FIG. 2 is an exemplary initial image which is input from a color CCD camera and stored in a memory.

FIG. 2 is an exemplary initial image which is input from the color CCD camera 80 and stored in the memory 100. The image shown in FIG. 2 is represented by a 640×480 array of pixels. There exist two kinds of normal white blood cells, i.e., neutrophils 210 and eosinophil 230 and immature granulocytes 220.

The significant feature of the present invention resides in recognizing blood cells based on a number of predetermined cell-characteristic parameters which can represent distinguishable features for each kind of blood cells. A procedure to implement the above feature of the present invention will be described in more detail with reference to FIG. 3.

Figure 3:
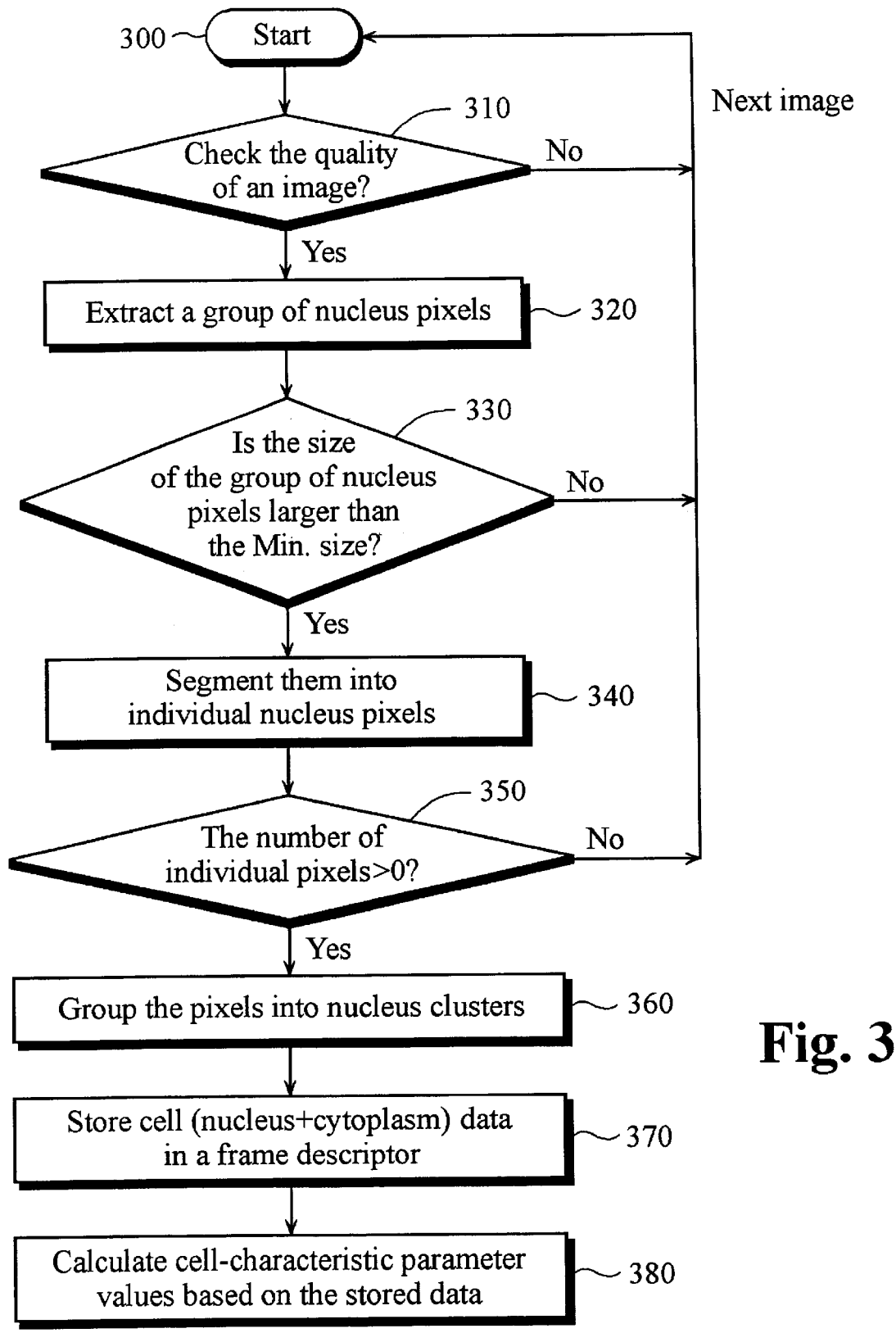
FIG. 3 is a logic flowchart illustrative of a process for extracting blood cells from image data and calculating cell-characteristic parameter values in accordance with the present invention.

FIG. 3 shows a logic flowchart illustrative of a process for extracting blood cells from the image data and calculating the cell characteristic parameter values for the extracted blood cells to recognize blood cells in accordance with the present invention. In step 310, the quality of the input image is first examined. If the input image is not recognizable since it is contaminated by some staining materials or is scratched so that it becomes difficult to analyze it, then the process goes to the next image. In accordance with the examination method of the present invention, the minimum value ($I^r_{min}$) and maximum value ($I^r_{max}$) of He, which is the sum of histograms for red, green, and blue color intensities within the image, are calculated according to the following equations, respectively.

$$\sum_{i=0}^{i=I^r_{min}} H_G(i) = 0.03 \cdot N_x \cdot N_y$$

$$\sum_{i=I^r_{min}}^{i=255} H_G(i) = 0.07 \cdot N_x \cdot N_y$$

$N_x$ and $N_y$ are related to the resolution of the image, and preferably their values are 640 and 480, respectively. If the difference between $I^r_{max}$ and $I^r_{min}$ (i.e., $I^r_{max}-I^r_{min}$) is less than a predetermined threshold, the current image is removed and the process starts to examine the next image. The threshold is 32 in the case that the resolution is 640×480 array of pixels and the magnification of the microscope is 500.

After the prescribed examination process has finished, the process proceeds to step 320 to extract a group of pixels forming the nucleus of each blood cell. The determination whether or not a given pixel is included in the nucleus group is made based on its green intensity value G(i) and the relationship between G(i) and its blue intensity value B(i). For any pixel in the image, if G(i) is less than the threshold of green intensity $G_{th}$ and G(i) is less than B(i), then the pixel is determined to be included in the nucleus group. On the other hand, if G(i) is more than or equal to $G_{th}$ or B(i), the pixel is determined not to be included in the nucleus group. The determination result is stored in the memory 100 to be used later. $G_{th}$ is represented as the following equation:

$$G_{th}=G^r_{min}+\Delta G \times K_G$$

wherein $\Delta G=G^r_{max}-G^r_{min}$, and $G^r_{max}$ and $G^r_{min}$ are upper and lower limits of the green intensity histogram, respectively, and these limits are green intensity values corresponding to 1% point from both ends of the histogram. $K_G$ is 0.2 as an experimental value in accordance with the present invention. $G^r_{min}$ and $G^r_{max}$ are represented as the following equations, where $H_G$ is the histogram distribution function of green intensity.

$$\sum_{i=0}^{i=G^r_{min}} H_G(i) = 0.01 \cdot N_x \cdot N_y$$

$$\sum_{i=G^r_{min}}^{i=255} H_G(i) = 0.01 \cdot N_x \cdot N_y$$

In step 320, the coordinates of pixels in the nucleus group extracted from the image are stored in the Nucleus Pixel Template (NPT) in the memory 100. The size of the nucleus group is compared with the predetermined minimum size in step 330. If the size of the nucleus group is less than the minimum size, it is determined to be too noisy and will be skipped. The process then proceeds to the start step 300 to examine the next image. If it is large enough, the nucleus group is segmented into individual nucleus pixels, and coordinates of the pixels and the associated data are stored in a nucleus blob list in the memory 100. In step 350, a decision is made as whether the number of the nucleus pixels is less than or equal to zero. If so, the process again goes back to the start step 300. If not, step 360 is performed for grouping the pixels into some nucleus clusters using the nucleus blob list. Each nucleus cluster is assumed to represent a different kind of blood cell. In accordance with the preferred embodiment of the present invention, a new algorithm is used together with a well-known hierarchical clustering algorithm. The new algorithm merges small clusters into a larger cluster and prevents large clusters from being merged together. For any pixel Bi, the pixel Bi is joined to a nucleus cluster C when the following relationship is satisfied between Bi and a pixel Bj in the cluster C:

$$Dij \leq Ri+Rj;$$

wherein Dij is the Euclidean distance between Bi and Bj, and each of Ri and Rj is an approximate radius calculated from the following equations using actual values $r_i$ and $r_j$:

$$Ri=r_i+r_i,\ r_i=-ar_i+b,$$

$$Rj=r_j+r_j,\ r_j=-ar_j+b;$$

wherein parameters a and b are determined based upon the resolution of the image. For example, when the magnification of the lens is 500 and the resolution is 640×480 array of pixels, a and b are 0.46 and 0.92, respectively.

In the process of extracting the nucleus pixels from the image, cytoplasm pixels which surround the nucleus pixels are also extracted from it. Assuming that a circle having a radius large enough to encircle nucleus pixels is drawn, other pixels not included in the circle are approximately decided as cytoplasm pixels. However, in the case that the shape of a blood cell is not accurate or the size of a nucleus is too small, the above decision method is not so reliable that an additional filtering process may be required. By calculating distances between color pixels and white pixels (i.e., background pixels), any pixel which is far from the colored pixels can be filtered out. In step 370, pixel data which are classified into nucleus and cytoplasm of a blood cell through the above steps are stored together in a frame descriptor in the memory.

Finally, for each blood cell stored in the frame descriptor, cell-characteristic parameter values are calculated based on the contents of the frame descriptor and, in step 380, they are stored in the memory. Cell-characteristic parameters are used in recognizing blood cells. Before starting the recognition process of actual blood cells, a number of cell-characteristic parameters which can represent the distinguishable feature of a blood cell are preselected according to the method of the present invention. To predetermine the cell-characteristic parameters, many experiments are conducted on a training set which includes many kinds of cells verified by experts, and the experimental results are analyzed according to a statistical translation methodology. In accordance with the present invention, 12 types of cell-characteristic parameters are predetermined. Assuming that any values on each of red, blue, and green intensity histograms are represented as r(i), b(i), and g(i), the cell-characteristic parameters Fi (i=1 ... 12) are represented as follows:

1. the difference between the ratios of red to blue in a nucleus and in cytoplasm;

$$F1 = \sum_{i \in nucl} r(i) \sum_{i \in nucl} b(i) - \sum_{i \in cyt} r(i) \sum_{i \in cyt} b(i)$$

2. the green-constrained ratio of red to blue in cytoplasm:

$$F2=\Sigma r(j)/\Sigma b(j);\ g(j)\leq \Sigma g(j)/Sc,\ j\in cyt\ (Sc\ \text{is the size of cytoplasm});$$

3. Cyan-coefficient of cytoplasm:

$$F3 = F2 - \sum_{i \in cyt} r(i) \sum_{i \in cyt} b(i);$$

4. the size of a nucleus:

$$F4=S_n;$$

5. the compactness of a nucleus:

$$F5 = \frac{4}{R^2}\left(\frac{Sn}{P}\right)^2$$

(R is the radius of a nucleus and P is the circumference of a nucleus)

6. an inclination degree at the start portion of the green intensity histogram ($HG_n$) of a nucleus;

$$F6 = \sum_{k=Gmin}^{Tgn} HG_n(k) \sum_{K=Gmin}^{Gmax} HG_n(k),\ Tgn = Kn(Gmax-Gmin)$$

(wherein the value of a control coefficient Kn is 0.06 in the case that the resolution is 640×480 pixels and the magnification of the microscope is 500. Further, Gmax and Gmin are respectively the maximum and minimum values of X coordinates in green intensity histogram);

7. the ratio of red to blue in cytoplasm:

$$F7 = \sum_{i \in cyt} r(i) \sum_{i \in cyt} bs(i),$$

$$bs(i) = b(i) - Bmin + 0.1(Bmax - Bmin)$$

(wherein Bmax and Bmin are respectively the maximum and minimum X coordinate values in blue intensity histogram);

8. the ratio of red to blue in a nucleus:

$$F8 = \sum_{i \in nucl} r(i) \sum_{i \in nucl} bs(i),$$

$$bs(i)=b(i)-Bmin+0.1\ (Bmax-Bmin);$$

9. the color tone of red to blue in cytoplasm:

$$F9 = \frac{1}{n}\sum_{i=1}^{n} \frac{r(i)-g(i)}{b(i)-g(i)},\ i \in \text{cytoplasm};$$

10. the deviation of green intensity in a nucleus:

$$F10 = \frac{1}{n}\sum_{i=1}^{n}(g(i)-\overline{g})^2,\ i \in nucl;$$

11. the deviation of red intensity in a nucleus:

$$F11 = \frac{1}{n}\sum_{i=1}^{n}(r(i)-\bar{r})^2, i \in nucl; \text{ and}$$

12. the smoothness of a nucleus;

$$F12 = \frac{1}{n}\sum_{i=1}^{n}(d(i)-\bar{d})^2, i \in nucl, d(i) = \overline{(x_i-x_c)^2+(y_i-y_c)^2}$$

($x_c$ and $Y_c$ are x and y coordinates representing the central point of a nucleus, respectively).

Cell-characteristic parameter values for each blood cell can be mapped onto particular locations in a multidimensional space with the parameters as its axes. In accordance with the present invention, by representing cell-characteristic parameter values for exemplary blood cells in a training set in the multidimensional space and analyzing the complex distribution status thereof, optimal cell-characteristic parameters can be selected from the above parameters. In order to find the optimal parameters, a minimum mean distance rule is applied. According to this rule, parameter values for the same kind of blood cell are located within a minimum mean distance in the multidimensional space. Accordingly, the multidimensional space can be reduced to a lower dimensional space using a multidimensional scaling technique so that optimal parameters can be found.

Figure 4A:
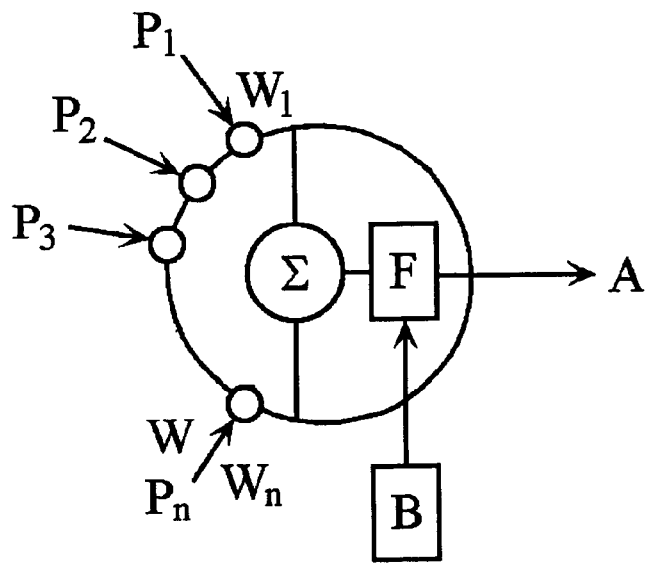
FIG. 4a shows a neuron within neural networks as a mathematical representation.
Figure 4B:
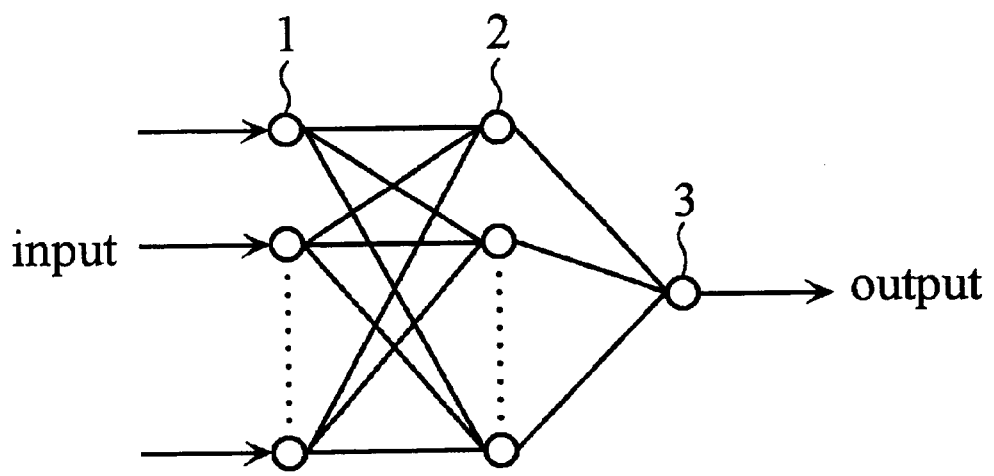
FIG. 4b shows a three-layer neural network employed in the present invention.

FIG. 4a shows a neuron within neutral networks as a mathematical representation, and FIG. 4b shows a three-layer neural network employed in the present invention. In one embodiment of the invention, a back propagation algorithm is used to reduce output errors. This algorithm calculates weights and biases of a neural network by reversely computing from an output layer (a first layer) to an input layer (a third layer). A response from the neural network is represented as a transfer function Fi below:

$$Ai = Fi[\Sigma(Wi \cdot Pi), Bi];$$

wherein i is a layer number, matrix Ai is an output vector, and Pi is an input vector. Further, Fi is a transfer function, matrices Wi and Bi are weights and biases, respectively, and Wi·Pi is the dot product thereof. The measurements of cell-characteristic parameters for target blood cells are inputted to the first layer. Then, results from a previous layer are automatically outputted to a next layer, and for example, results from the first layer are outputted to the second layer. Accordingly, an output $A_3$ at the third layer is calculated according to the following equations:

$$A_1 = F_1(W_1, P_1, B_1);$$

$$A_2 = F_2(W_2, A_1, B_2);$$

and $$A_3 = F_2(W_1, A_2, B_3).$$

The transfer function Fi is represented as a function of W, P, and B. A sigmoidal transfer function is used in the embodiment to resolve the non-linear feature of data representing the shape and color information of blood cells in a multidimensional space. The sigmoidal transfer function Fi is represented as below:

$$Fi = 1/(1+e^{-(\Sigma Wi \cdot Pi)+Bi}).$$

An adaptive learning rate and momentum technique is used for calculating the weight matrix W and bias matrix B. According to this technique, optimal weight and bias matrices are calculated by minutely modifying their values in order to reduce output errors. This technique analyzes complex curved surfaces, especially deep-curved surfaces, formed in a multidimensional space so that optimal weight and bias matrices can be calculated more rapidly and efficiently.

Figure 5:
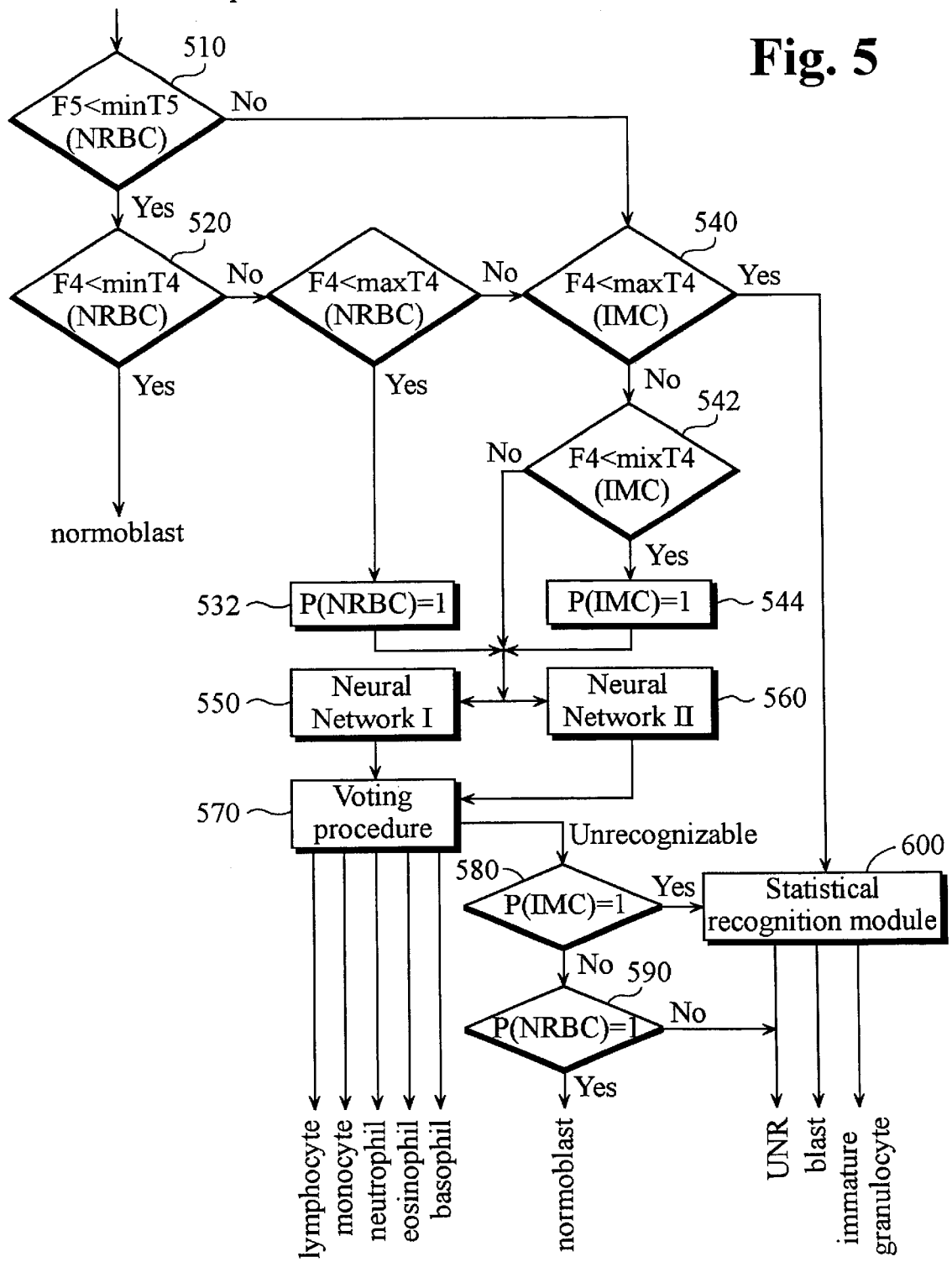
FIG. 5 illustrates a logic flowchart for recognizing blood cells using two neural networks and a statistical recognition module in accordance with a preferred embodiment of the present invention.

FIG. 5 illustrates a logic flowchart for recognizing blood cells using two neural networks and a statistical recognition module in accordance with a preferred embodiment of the present invention. Two neural networks 550 and 560 are utilized in recognizing blood cells based on their cell-characteristic parameter values. These two neural networks are optimal networks selected from about 70 kinds of heterogeneous 3-layer neural networks having different numbers of neurons. Such various kinds of neural networks are examined through the recognition experimentation with a large number of blood cells, and the recognition error rates thereof are compared so that two optimal neural networks can be found among them. In one embodiment of the present invention, the first neural network 550 has the recognition error rate 5.9% and the second neural network 560 has the recognition error rate 6.5%. A voting procedure is further introduced to select between the better results from the first and second networks so that the recognition correctness can be improved.

The cell-recognition procedure according to the present invention is described below with reference to FIG. 5. First, in step 510, a comparison is made between the F5 value of a target blood cell in the image data and the minimum F5 value of a normoblast, minT5(NRBC), which has been stored as one of the criteria in the memory 100. As previously described, F5 is a cell-characteristic parameter and represents the compactness of a nucleus. If the F5 value of the target blood cell is less than minT5(NRBC), then the control passes to step 540 where another comparison is made between F4 (nucleus size) of the target and the minimum F4 value of a normoblast, minT4(NRBC). Also, minT4(NRBC) has been already stored as one of the criteria in the memory. If the F4 value of the target cell is less than the minimum value, then the target cell is recognized as a normoblast and the recognition procedure ends. If not, the F4 value of the target cell is compared with the maximum F4 value of a normoblast, maxT4(NRBC), in step 530. If the target cell F4 is less than the maxT4(NRBC), the target cell is roughly assumed to be a normoblast and the probability of a normoblast, P(NRBC), is set to 1. To exactly recognize blood cells, special recognition steps 550 and 560 using two neural networks are performed.

In the case that the F5 value of the target cell is not less than the minT5(NRBC) or the F4 value of the target cell is not less than the maxT4(NRBC), the control passes to step 540. In step 540, the F4 value of the target cell is compared with the maximum F4 value of immature cells such as an immature granulocyte or a blast, maxT4(IMC). If it is more than maxT4(IMC), a statistical recognition step 600 for determining whether the target cell is a blast or an immature granulocyte is performed (the statistical recognition step 600 will be described in detail later). Otherwise, it is compared with the minimum F4 value of an immature cell, minT4(IMC), in step 542. If it is more than minT4(IMC), then the target cell is approximately assumed to be an immature cell and the probability of an immature cell, P(IMC), is set to 1 in step 544. In this case, further recognition steps 550 and 560 are required to better recognize the target cell.

A voting procedure 570 for combining recognition results from the first and second neural networks is performed. If both results are same, the target cell is determined. For example, if both results are (1 0 0 0 0), then the target cell is recognized as a lymphocyte, and if they are (0 0 0 0 1), then it is recognized as a basophil.

On the contrary, if two results are not the same, the target cell is determined as unrecognizable and additional recognition step are performed. First, in step 580, a determination is made as to whether the target cell has the probability of immature cells (i.e., P(IMC)=1). If not, another determination is made as whether the target cell has the probability of a normoblast (i.e., P(NRBC)=1). If P(NRBC)=1, the target cell is recognized as a normoblast and the recognition process ends. Otherwise, the target cell is finally determined as an unrecognizable cell (UNR).

If it is determined that the target cell has the probability of immature cells in step 580, then the statistical recognition step 600 is further performed. The statistical recognition method according to the present invention is used for recognizing a blast and an immature granulocyte using the following decision rule:

$$d_x = \Sigma \alpha i F i + \alpha 0, \ \Sigma \alpha i = 1$$

wherein $d_k$ means a linear discriminant for separating each kind of cell cluster. $\alpha i$ and $\beta 0$ are experimental values obtained from the scope and distribution of cell-characteristic parameter (Fi) values for each kind of cell in a training set. The image data and recognition results of target blood cells are stored in the memory 100 so that they may be reexamined whenever necessary. They are further used in calculating weights and biases of neural networks which are employed in the present invention.

In accordance with the present invention, it is possible to perform a more rapid and objective blood cell recognition. Compared with the previous recognition method, recognition exactness is improved through using two neural networks, and even immature cells can be recognized by the apparatus of the present invention.

While the invention has been described with respect to the particular embodiment above, it will be understood by those skilled in the art that modifications may be made without departing from the spirit and scope of the present invention. This embodiment is for the purpose of example and illustration only, and is not to be taken to limit the scope of the invention narrower than the scope of the appended claims.

What is claimed is:

1. A method for automatically recognizing blood cells, said method comprising:

obtaining image data of said blood cells;

storing the image data of said blood cells in a memory;

analyzing the image data of said blood cells and calculating a plurality of cell-characteristic parameter values for each of said blood cells in the image data; and recognizing each of said blood cells based on said plurality of cell-characteristic parameter values, wherein said analyzing step comprises the steps of:

extracting a group of nucleus pixels from said stored image data and storing said group of nucleus pixel data in the memory;

segmenting said group of nucleus pixels into individual nucleus clusters which represent each of said blood cells, and storing each individual nucleus cluster and associated cytoplasm data in the memory; and calculating cell-characteristic parameter values for each of said blood cells based on the stored nucleus cluster and associated cytoplasm data.

2. The method according to claim 1, wherein the types of said plurality of cell-characteristic parameters are predetermined and each of said plurality of cell-characteristic parameters represents the shape and color of the blood cells.

3. The method according to claim 1, wherein said recognizing step comprises detecting normoblast cells according to one of said cell-characteristic parameters which represent the size of the blood cell.

4. The method according to claim 3, wherein said recognizing step further comprises inputting said cell-characteristic parameter values of each of said blood cells, which are not recognized as normoblast cells, to at least two neural networks, and determining the kind of each of said blood cells as a normal white blood cell selected from a group consisting of neutrophils, lymphocytes, monocytes, basophils, and eosinophils when outputs from said neural networks are the same, and determining the kind of each of said blood cells as an immature cell when the outputs from said neural networks are not the same.

5. The method according to claim 4, wherein each of said neural network has an input layer, a hidden layer, and an output layer, and weights and biases at the hidden layer of each neural network are determined by reversely calculating input values from outputs of the output layers.

6. An apparatus for automatically recognizing blood cells, said method comprising:

means for obtaining image data of said blood cells;

means for storing the image data of said blood cells in a memory;

means for analyzing the image data of said blood cells and calculating a plurality of cell-characteristic parameter values for each of said blood cells in the image data; and means for recognizing each of said blood cells based on said plurality of cell-characteristic parameter values, wherein said analyzing and calculating means comprises:

means for extracting a group of nucleus pixels from said stored image data and storing said group of nucleus pixel data in the memory;

means for segmenting said group of nucleus pixels into individual nucleus clusters which represent each of said blood cells, and storing each individual nucleus cluster and associated cytoplasm data in the memory; and means for calculating cell-characteristic parameter values for each of said blood cells based on the stored nucleus cluster and associated cytoplasm data.

* * * * *